June 15, 1965 G. H. FUJII Plant Pat. 2,537
VERBENA PERUVIANA PLANT
Filed Nov. 1, 1963
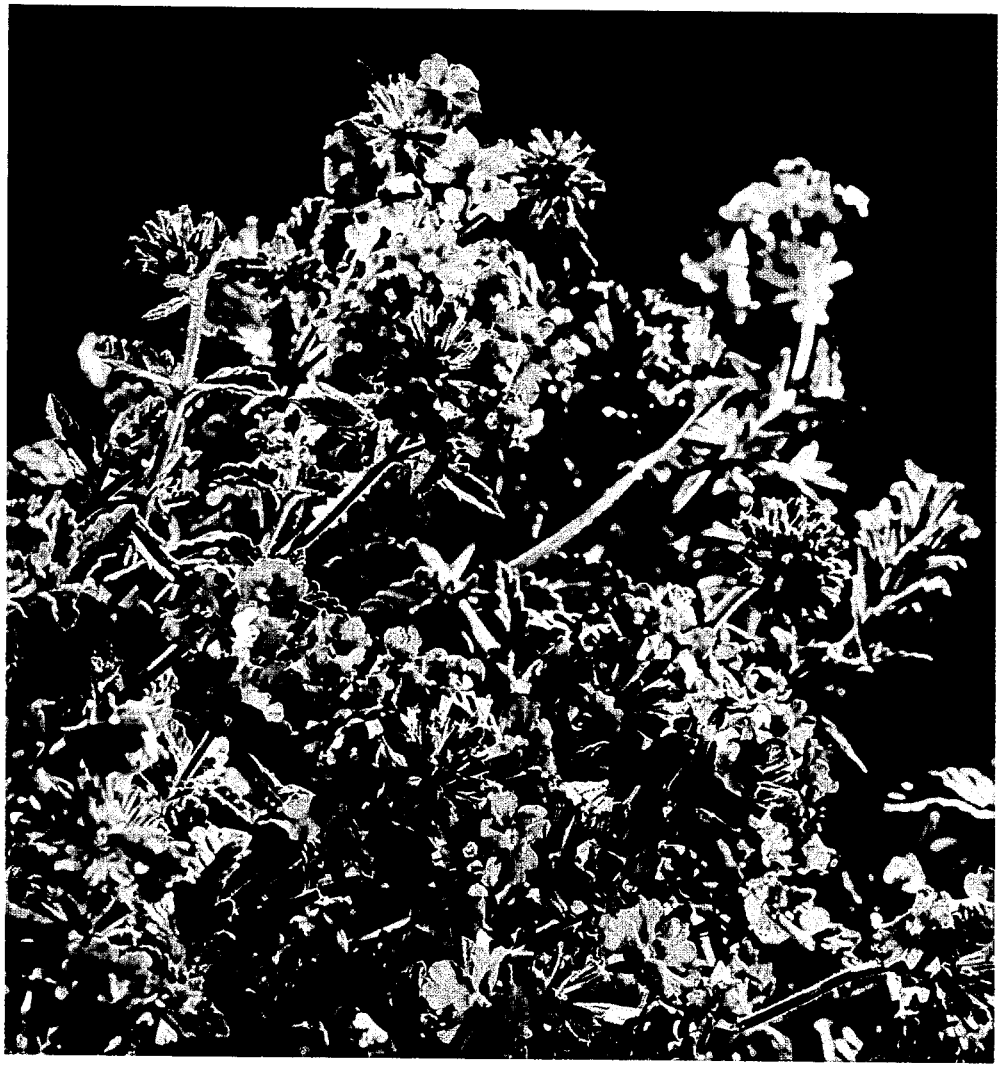
INVENTOR
GEORGE H. FUJII
BY J. F. Cuneo
ATTORNEY United States Patent Office Plant Pat. 2,537
Patented June 15, 1965

2,537
*VERBENA PERUVIANA* PLANT

George H. Fujii, 16711 S. Berendo, Gardena, Calif.

Filed Nov. 1, 1963, Ser. No. 320,974
1 Claim. (Cl. Plt.—87)

This invention relates to a new and distinct variety of Verbena plant of the prostrate type.

The new and distinct variety is characterized by its unique violet purple blooms that are borne in large clusters on a long stiff stem; by its rather thick, bright green leaves, and its prostrate and spreading habit that makes excellent ground cover. The new variety exhibits a vigorous and hardy growth.

The new and distinct variety was discovered by me as a stem sport growing in a cultivated bed of a light pink unpatented variety of Verbena plant that is situated in my growing grounds located at 554 East 165th Street, city of Gardena, county of Los Angeles, State of California. This sport was discovered by me in June of 1960 and differs from its parent plant in that the flowers are a violet purple shade where those of the parent plant are a light pink. The new variety has been reproduced asexually at 554 East 165th Street, Gardena, California, from cuttings and all of the descendants of this plant have exhibited the distinguishing color and other characteristics of this new and distinct variety, and have thereby established that the strain is true. A large number of cuttings have been made since the new variety was discovered. The new variety cannot be reproduced true from seed.

The accompanying illustration, in full color, shows typical specimens of the flowers and leaves. The colors appearing in the illustration are as nearly correct as it is possible to reproduce them by this type of illustration. To facilitate the identification of the important colors referred to in the specification, the nomenclature adopted by the British Horticultural Colour Charts has been followed. A detailed description of the plant and flowers of the new variety of Verbena plant follows:

*The flower*

Localtiy where grown and observed: Gardena, California.

Flowers borne: Clusters of individual flowers are borne on stiff substantially erect stems; the length of the stems varies considerably but the longest are about eight inches.

Size of clusters: The flowers are arranged in the form of a rough circle that ranges from two to two and one-eighth inches in diameter.

Individual flowers:

*Size; shape.*—Each individual flower has usually five petals and varies from ⅝" to ¾" in diameter across the widest portion. The rather large, brightly colored violet purple flowers create a striking display when the plants are fully in bloom.

*Color.*—The outer portions of each flower can be best described as Petunia Purple 32. The inner portions of the flower approaching the center merge into a shade of purple that is identified as Beetroot Purple that falls between the 830 and the 830/1 shade. The center of the flower has a small eye that is Uranium Green 63/2.

*The plant*

Habit: The plant is of the prostrate type, exhibits a vigorous growth and provides excellent ground cover.

Blooming period: The plant blooms profusely from February to November in the particular area where it has been observed. The blooming period extends into the very late fall in years where the weather remains warm beyond September as is frequently the case in southern California.

Leaves:

*Shape.*—Leaves are ovate and some might be classed as oblong triangular. The leaves have a substantially cuneate base that is decurrent into a rather short petiole; in some leaves the attachment could be classed as sessile. Divisions of the leaves are pinnatified into linear acute lobes. The leaves have prominant veins, particularly on the underside.

*Texture.*—The leaves are relatively thick and are veiny and rugose.

*Borne on stem.*—The leaves are predominantly opposite.

*Size.*—Length—leaves are one and one-quarter inches in length. Width—the widest portion of the leaf occurs near the base and is usually three quarters of an inch across the widest portion. The width of the narrower portion of the leaf which commences above the widest portion is about one half inch, this width tapers to a narrow point as it reaches the outer end of the leaf.

*Color.*—Upper side—Parsley Green oo962. Underside—Parsley Green oo962/1.

Branches: Branches remain close to the ground and extend in all directions from the central portion of the plant.

Rooting: The plant may be classed as self rooting.

Aroma: The blooms have no appreciable aroma. The foliage in certain times of the year has a very slight aroma.

I claim:

A new and distinct variety of Verbena plant substantially as illustrated and described, characterized by its violet-purple individual flowers with the outer portion of the flower Petunia Purple and with the central portion of the flower that merges into Beetroot Purple surrounding the central yellow-green eye, by its cluster of many flowers borne on stiff erect stems, by its bright green leaves that are opposite each other on the stems, and by its vigorous growth.

No references cited.

ABRAHAM G. STONE, *Primary Examiner.*